United States Patent [19]

Krause et al.

[11] Patent Number: 5,689,032

[45] Date of Patent: Nov. 18, 1997

[54] METHOD AND APPARATUS FOR RECOVERY OF $H_2$ AND $C_2$ AND HEAVIER COMPONENTS

[75] Inventors: William A. Krause; Ronald C. Pasadyn, both of Houston, Tex.

[73] Assignee: Krause/Pasadyn, a Partnership, Houston, Tex.

[21] Appl. No.: 343,784

[22] Filed: Nov. 22, 1994

[51] Int. Cl.⁶ .................... C07C 7/00; C10G 49/22; F25J 3/00
[52] U.S. Cl. .................... 585/802; 585/800; 208/100; 208/102; 208/103; 208/104; 62/9; 62/11; 62/23
[58] Field of Search .................... 585/802, 800; 208/100, 102, 103, 104; 62/9, 11, 23

[56] References Cited

U.S. PATENT DOCUMENTS

| | | |
|---|---|---|
| 4,617,039 | 10/1986 | Buck . |
| 4,740,222 | 4/1988 | Mehra . |
| 4,743,282 | 5/1988 | Mehra . |
| 4,832,718 | 5/1989 | Mehra . |
| 4,895,584 | 1/1990 | Buck et al. . |
| 4,925,573 | 5/1990 | Vorlow .................... 208/100 |
| 5,019,143 | 5/1991 | Mehrta . |

OTHER PUBLICATIONS

Chemical Engineering Magazine, "Reengineering Ethylene's Cold Train,", 37–39 (Jan. 1994).

Oil & Gas Journal, "Olefin Recovery from FCC Offgas Can Pay Off," 94, 96–98, (Apr. 1992).

Energy Progress, "*Recover Valuable Off-Gases by the Braun ROE Process*," vol. 6, No. 4, 205–209, (Dec. 1986).

Kinetics Technology Int'l Corp., "*Advanced Ethylene Process*," 14 page report, (Mar. 1993).

Advanced Extraction Technologies, Inc. (Unpublished), "*Non–Cryogenic Absorption–Based Mehra Process Technology Upgrades Hugoton Gases*", 18 page report, (Mar. 1993).

*Primary Examiner*—Glenn A. Caldarola
*Assistant Examiner*—In Suk Bullock
*Attorney, Agent, or Firm*—Vaden, Eickenroht & Thompson, L.L.P.

[57] ABSTRACT

A process and apparatus for separating a hydrocarbon gas into fractions containing predominant portions of hydrogen, methane, and $C_2$ and heavier components, where the methane and lighter components are separated from the feed gas under non-cryogenic conditions to produce a hydrogen-rich fraction, a first fraction rich in $C_2$ and heavier components and a hydrocarbon-rich fraction, the hydrocarbon-rich fraction then being separated under cryogenic conditions into a second fraction rich in $C_2$ and heavier components and a methane-rich fraction.

13 Claims, 15 Drawing Sheets

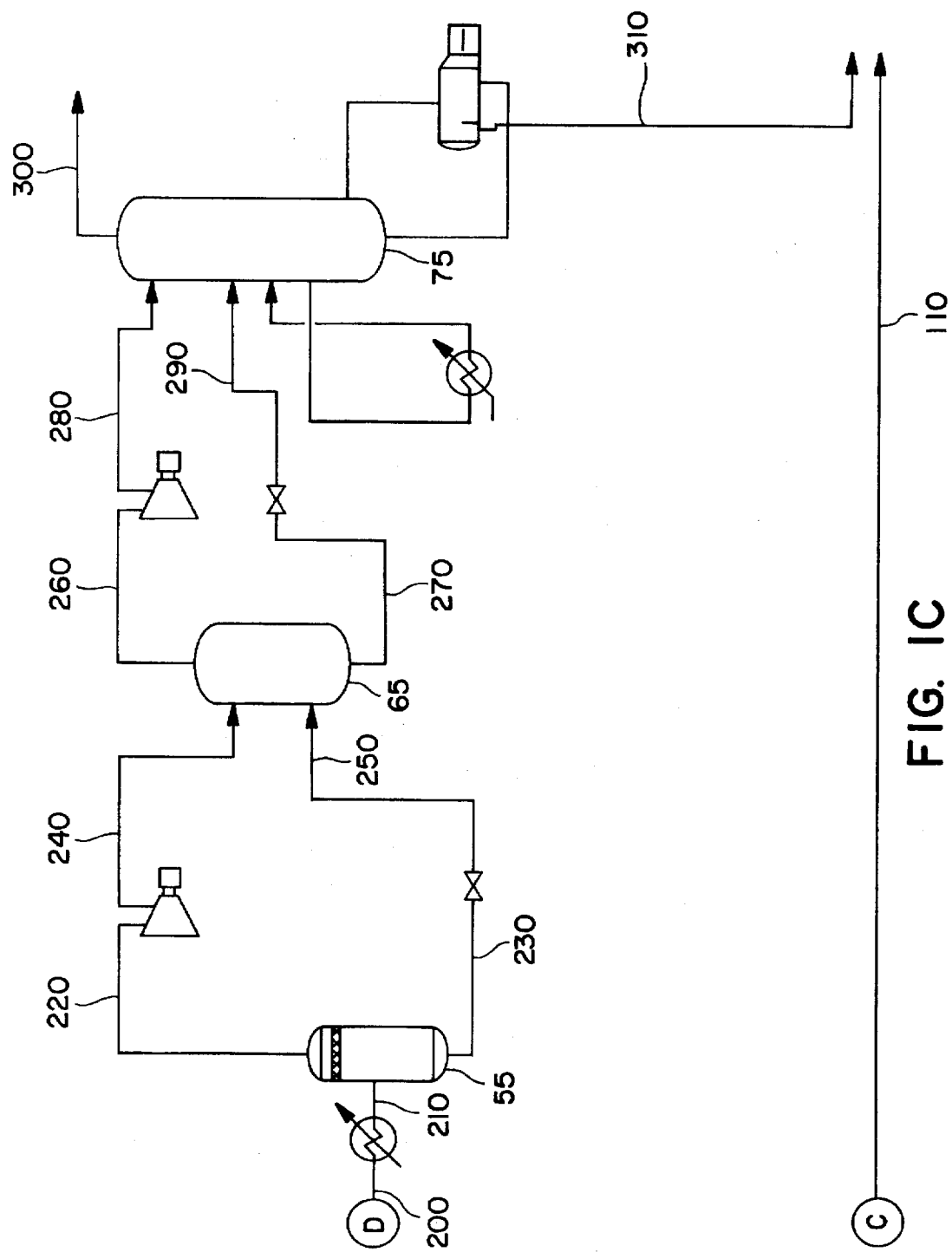
FIG. IC

Fig. 3A
Table A

| STREAM/ DESCRIPTION | UNIT | 10 | 20 | 30 |
|---|---|---|---|---|
| Vapour Frac | | 0.9797 | 0.7408 | 1.0000 |
| Temperature | °F | 120.7965 | -15.0000 | 110.0000 |
| Pressure | psia | 860.0001 | 840.0001 | 835.0001 |
| Molar Flow | lbmole/hr | 11703.6552 | 11703.6552 | 8670.4975 |
| Mass Flow | lb/hr | 233582.8126 | 233582.8126 | 117083.9722 |
| Liq.Vol.Flow | Barrel/day | 45018.3390 | 45018.3390 | 28120.2040 |
| Enthalpy | Btu/hr | 4.87239E+07 | 1.68503E+07 | 3.49350E+07 |
| Density | lb/ft3 | 3.1329 | 3.1329 | 1.9183 |
| Mole Wt | | 19.9581 | 19.9581 | 13.5037 |
| Spec. Heat | Btu/lbmole-F | 12.5550 | 12.5550 | 9.3756 |
| Therm Cond. | Btu/hr-ft-F | --- | --- | 0.0413 |
| Viscosity | cP | --- | --- | 0.0131 |
| Z Factor | | --- | --- | 0.9615 |
| Sur Tension | dyne/cm | --- | --- | --- |
| Std Density | lb/ft3 | --- | --- | --- |
| Hydrogen | lbmole/hr | 3568.4158 | 3568.4158 | 3507.4744 |
| Nitrogen | lbmole/hr | 416.9403 | 416.9403 | 399.7212 |
| CO | lbmole/hr | 29.3336 | 29.3336 | 27.8867 |
| Methane | lbmole/hr | 3813.4625 | 3813.4625 | 3316.1161 |
| Ethylene | lbmole/hr | 553.6853 | 553.6853 | 345.0690 |
| Ethane | lbmole/hr | 1817.0770 | 1817.0770 | 911.4036 |
| Propene | lbmole/hr | 99.1490 | 99.1490 | 23.5144 |
| Propane | lbmole/hr | 498.6962 | 498.6962 | 101.5408 |
| 1-Butane | lbmole/hr | 124.4151 | 124.4151 | 11.0649 |
| n-Butane | lbmole/hr | 103.3681 | 103.3681 | 6.7863 |
| 1-Butene | lbmole/hr | 157.3502 | 157.3502 | 11.7521 |
| 1-Pentane | lbmole/hr | 147.7174 | 147.7174 | 3.7078 |
| n-Pentane | lbmole/hr | 49.0164 | 49.0164 | 0.8792 |
| 1-Pentene | lbmole/hr | 115.2131 | 115.2131 | 2.9860 |
| n-Hexane | lbmole/hr | 89.7186 | 89.7186 | 0.4802 |
| $H_2O$ | lbmole/hr | 71.6476 | 71.6476 | 0.1146 |
| E Glycol | lbmole/hr | 48.4488 | 48.4488 | 0.0002 |

Fig. 3B
Table A

| STREAM/ DESCRIPTION | UNIT | 40 | 50 | 60 |
|---|---|---|---|---|
| Vapour Frac | | 0.0000 | 0.0000 | 0.0695 |
| Temperature | °F | -15.0000 | -15.0000 | -18.6644 |
| Pressure | psia | 840.0001 | 840.0001 | 475.0000 |
| Molar Flow | lbmole/hr | 2913.1752 | 119.9825 | 2913.1752 |
| Mass Flow | lb/hr | 112203.1601 | 4295.6776 | 112203.1601 |
| Liq.Vol.Flow | Barrel/day | 16624.2927 | 273.8433 | 16624.2927 |
| Enthalpy | Btu/hr | -5.45449E+06 | -2.46140E+06 | -5.45449E+06 |
| Density | lb/ft3 | --- | 70.6456 | --- |
| Mole Wt | | 38.5157 | 35.8025 | 38.5157 |
| Spec. Heat | Btu/lbmole-F | --- | 24.2842 | --- |
| Therm Cond. | Btu/hr-ft-F | --- | 0.2494 | --- |
| Viscosity | cP | --- | 26.2663 | --- |
| Z Factor | | --- | 0.0892 | --- |
| Sur Tension | dyne/cm | --- | 60.0612 | --- |
| Std Density | lb/ft3 | --- | 68.4482 | --- |
| Hydrogen | lbmole/hr | 0.0209 | 0.0222 | 0.0209 |
| Nitrogen | lbmole/hr | 0.0059 | 0.0197 | 0.0059 |
| CO | lbmole/hr | 0.0005 | 0.0003 | 0.0005 |
| Methane | lbmole/hr | 0.1707 | 0.0007 | 0.1707 |
| Ethylene | lbmole/hr | 0.0716 | 0.0000 | 0.0716 |
| Ethane | lbmole/hr | 0.3109 | 0.0000 | 0.3109 |
| Propene | lbmole/hr | 0.0260 | 0.0000 | 0.0260 |
| Propane | lbmole/hr | 0.1363 | 0.0000 | 0.1363 |
| 1-Butane | lbmole/hr | 0.0389 | 0.0000 | 0.0389 |
| n-Butane | lbmole/hr | 0.0332 | 0.0000 | 0.0332 |
| 1-Butene | lbmole/hr | 0.0500 | 0.0000 | 0.0500 |
| 1-Pentane | lbmole/hr | 0.0494 | 0.0000 | 0.0494 |
| n-Pentane | lbmole/hr | 0.0165 | 0.0000 | 0.0165 |
| 1-Pentene | lbmole/hr | 0.0385 | 0.0000 | 0.0385 |
| n-Hexane | lbmole/hr | 0.0306 | 0.0000 | 0.0306 |
| $H_2O$ | lbmole/hr | 1.432E-05 | 71.4913 | 1.432E-05 |
| E Glycol | lbmole/hr | 1.077E-07 | 48.4483 | 1.077E-07 |

Fig. 3C
Table A

| STREAM/DESCRIPTION | UNIT | 70 | 80 | 90 |
|---|---|---|---|---|
| Vapour Frac | | 1.0000 | 0.0000 | 0.0000 |
| Temperature | °F | -12.5139 | 130.0700 | 130.8695 |
| Pressure | psia | 450.0000 | 460.0000 | 500.0000 |
| Molar Flow | lbmole/hr | 781.8032 | 2131.3720 | 2131.3720 |
| Mass Flow | lb/hr | 15079.5383 | 97123.6272 | 97123.6272 |
| Liq.Vol.Flow | Barrel/day | 3144.7345 | 13479.5581 | 13479.5581 |
| Enthalpy | Btu/hr | 2.46509E+06 | 2.41548E+06 | 2.44921E+06 |
| Density | lb/ft3 | 2.4356 | 28.4177 | 28.3598 |
| Mole Wt | | 19.2878 | 45.5686 | 45.5686 |
| Spec. Heat | Btu/lbmole F | 11.7479 | 34.7403 | 34.7483 |
| Therm Cond. | Btu/hr-ft-F | 0.0292 | 0.0326 | 0.0326 |
| Viscosity | cP | 0.0150 | 0.0772 | 0.0772 |
| Z Factor | | 0.9320 | 0.1166 | 0.1166 |
| Sur Tension | dyne/cm | --- | 4.4340 | 4.4340 |
| Std Density | lb/ft3 | --- | 32.6537 | 32.6537 |
| Hydrogen | lbmole/hr | 60.9191 | 0.0000 | 0.0000 |
| Nitrogen | lbmole/hr | 17.1994 | 0.0000 | 0.0000 |
| CO | lbmole/hr | 1.4466 | 0.0000 | 0.0000 |
| Methane | lbmole/hr | 497.3299 | 0.0159 | 0.0159 |
| Ethylene | lbmole/hr | 49.8183 | 158.7980 | 158.7980 |
| Ethane | lbmole/hr | 132.4415 | 773.2320 | 773.2320 |
| Propene | lbmole/hr | 3.2142 | 72.4204 | 72.4204 |
| Propane | lbmole/hr | 14.2866 | 382.8688 | 382.8688 |
| 1-Butane | lbmole/hr | 1.5086 | 111.8416 | 111.8416 |
| n-Butane | lbmole/hr | 0.9187 | 95.6631 | 95.6631 |
| 1-Butene | lbmole/hr | 1.6266 | 143.9715 | 143.9715 |
| 1-Pentane | lbmole/hr | 0.4946 | 143.5150 | 143.5150 |
| n-Pentane | lbmole/hr | 0.1167 | 48.0205 | 48.0205 |
| 1-Pentene | lbmole/hr | 0.4044 | 111.8227 | 111.8227 |
| n-Hexane | lbmole/hr | 0.0617 | 89.1767 | 89.1767 |
| $H_2O$ | lbmole/hr | 0.0162 | 0.0255 | 0.0255 |
| E Glycol | lbmole/hr | 0.0000 | 0.0003 | 0.0003 |

Fig. 3D
Table A

| STREAM/ DESCRIPTION | UNIT | 100 | 110 | 120 |
|---|---|---|---|---|
| Vapour Frac | | 1.0000 | 0.0000 | 0.0000 |
| Temperature | °F | 216.8281 | 130.8695 | 120.0000 |
| Pressure | psia | 855.0001 | 495.0000 | 100.0000 |
| Molar Flow | lbmole/hr | 781.8032 | 2131.3462 | 0.0258 |
| Mass Flow | lb/hr | 15079.5383 | 97123.1449 | 0.4784 |
| Liq.Vol.Flow | Barrel/day | 3144.7345 | 13479.5259 | 0.0327 |
| Enthalpy | Btu/hr | 4.25475E+06 | 2.45224E+06 | -364.5222 |
| Density | lb/ft3 | 2.4355 | 28.3596 | 62.0796 |
| Mole Wt | | 19.2882 | 45.5689 | 18.5246 |
| Spec. Heat | Btu/lbmole-F | 11.7480 | 34.5404 | 18.8238 |
| Therm Cond. | Btu/hr-ft-F | 0.0292 | 0.0324 | 0.3677 |
| Viscosity | cP | 0.0150 | 0.0771 | 0.6389 |
| Z Factor | | 0.9327 | 0.1255 | 0.0048 |
| Sur Tension | dyne/cm | --- | 4.4066 | 66.9882 |
| Std Density | lb/ft3 | --- | 32.6536 | 63.6142 |
| Hydrogen | lbmole/hr | 60.9191 | 0.0000 | 0.0000 |
| Nitrogen | lbmole/hr | 17.1994 | 0.0000 | 0.0000 |
| CO | lbmole/hr | 1.4466 | 0.0000 | 0.0000 |
| Methane | lbmole/hr | 497.3299 | 0.0159 | 0.0000 |
| Ethylene | lbmole/hr | 49.8183 | 158.7980 | 0.0000 |
| Ethane | lbmole/hr | 132.4415 | 773.2320 | 0.0000 |
| Propene | lbmole/hr | 3.2142 | 72.4204 | 0.0000 |
| Propane | lbmole/hr | 14.2866 | 382.8688 | 0.0000 |
| 1-Butane | lbmole/hr | 1.5086 | 111.8416 | 0.0000 |
| n-Butane | lbmole/hr | 0.9187 | 95.6631 | 0.0000 |
| 1-Butene | lbmole/hr | 1.6266 | 143.9716 | 0.0000 |
| 1-Pentane | lbmole/hr | 0.4946 | 143.5150 | 0.0000 |
| n-Pentane | lbmole/hr | 0.1167 | 48.0205 | 0.0000 |
| 1-Pentene | lbmole/hr | 0.4044 | 111.8227 | 0.0000 |
| n-Hexane | lbmole/hr | 0.0617 | 89.1767 | 0.0000 |
| $H_2O$ | lbmole/hr | 0.0162 | 0.0000 | 0.0255 |
| E Glycol | lbmole/hr | 0.0000 | 0.0000 | 0.0003 |

Fig. 3E
Table A

| STREAM/ DESCRIPTION | UNIT | 130 | 140 | 150 |
|---|---|---|---|---|
| Vapour Frac |  | 1.0000 | 1.0000 | 1.0000 |
| Temperature | °F | 176.0000 | 176.0000 | 176.0000 |
| Pressure | psia | 830.0001 | 115.0000 | 810.0001 |
| Molar Flow | lbmole/hr | 8670.1525 | 3118.1957 | 5551.9562 |
| Mass Flow | lb/hr | 117074.4993 | 11971.9565 | 105102.5310 |
| Liq.Vol.Flow | Barrel/day | 28118.5087 | 6786.4798 | 21332.0248 |
| Enthalpy | Btu/hr | 4.03500E+07 | 1.12926E+07 | 2.73470E+07 |
| Density | lb/ft3 | 1.6787 | 0.0646 | 2.4095 |
| Mole Wt |  | 13.5032 | 3.8394 | 18.9307 |
| Spec. Heat | Btu/lbmole-F | 9.5424 | 7.1339 | 11.0719 |
| Therm Cond. | Btu/hr-ft-F | 0.0454 | 0.0975 | 0.0290 |
| Viscosity | cP | 0.0140 | 0.0103 | 0.0146 |
| Z Factor |  | 0.9787 | 1.0022 | 0.9329 |
| Sur Tension | dyne/cm | --- | --- | --- |
| Std Density | lb/ft3 | --- | --- | --- |
| Hydrogen | lbmole/hr | 3507.4643 | 2808.0759 | 699.3884 |
| Nitrogen | lbmole/hr | 399.7199 | 22.7840 | 376.9359 |
| CO | lbmole/hr | 27.8864 | 3.0173 | 24.8691 |
| Methane | lbmole/hr | 3316.0183 | 214.2148 | 3101.8036 |
| Ethylene | lbmole/hr | 345.0320 | 21.2195 | 323.8125 |
| Ethane | lbmole/hr | 911.2645 | 43.0117 | 868.2529 |
| Propene | lbmole/hr | 23.5081 | 1.0673 | 22.4408 |
| Propane | lbmole/hr | 101.5115 | 4.3751 | 97.1363 |
| 1-Butane | lbmole/hr | 11.0609 | 0.2666 | 10.7943 |
| n-Butane | lbmole/hr | 6.7837 | 0.1635 | 6.6202 |
| 1-Butene | lbmole/hr | 11.7476 | 0.0000 | 11.7476 |
| 1-Pentane | lbmole/hr | 3.7062 | 0.0000 | 3.7062 |
| n-Pentane | lbmole/hr | 0.8788 | 0.0000 | 0.8788 |
| 1-Pentene | lbmole/hr | 2.9847 | 0.0000 | 2.9847 |
| n-Hexane | lbmole/hr | 0.4799 | 0.0000 | 0.4799 |
| $H_2O$ | lbmole/hr | 0.1054 | 0.0000 | 0.1054 |
| E Glycol | lbmole/hr | 0.0002 | 0.0000 | 0.0002 |

Fig. 3F
Table A

| STREAM/ DESCRIPTION | UNIT | 160 | 170 | 180 |
|---|---|---|---|---|
| Vapour Frac |  | 1.0000 | 1.0000 | --- |
| Temperature | °F | 181.0071 | 120.0000 | --- |
| Pressure | psia | 810.0001 | 805.0002 | --- |
| Molar Flow | lbmole/hr | 6333.8825 | 6333.8825 | 0.1200 |
| Mass Flow | lb/hr | 120184.1393 | 120184.1393 | 2.1710 |
| Liq.Vol.Flow | Barrel/day | 24477.2235 | 24477.2235 | 0.1489 |
| Enthalpy | Btu/hr | 3.16023E+07 | 2.41548E+06 | --- |
| Density | lb/ft3 | 2.3954 | 2.7238 | --- |
| Mole Wt |  | 18.9748 | 18.9748 | 18.1520 |
| Spec. Heat | Btu/lbmole-F | 11.1436 | 11.0639 | --- |
| Therm Cond. | Btu/hr-ft-F | 0.0290 | 0.0264 | --- |
| Viscosity | cP | 0.0146 | 0.0137 | --- |
| Z Factor |  | 0.9332 | 0.9015 | --- |
| Sur Tension | dyne/cm | --- | --- | --- |
| Std Density | lb/ft3 | --- | --- | --- |
| Hydrogen | lbmole/hr | 760.3160 | 760.3160 | 0.0000 |
| Nitrogen | lbmole/hr | 394.1382 | 394.1382 | 0.0000 |
| CO | lbmole/hr | 26.3160 | 26.3160 | 0.0000 |
| Methane | lbmole/hr | 3599.2310 | 3599.2310 | 0.0000 |
| Ethylene | lbmole/hr | 373.6366 | 373.6366 | 0.0000 |
| Ethane | lbmole/hr | 1000.7051 | 1000.7051 | 0.0000 |
| Propene | lbmole/hr | 25.6550 | 25.6550 | 0.0000 |
| Propane | lbmole/hr | 111.4224 | 111.4224 | 0.0000 |
| 1-Butane | lbmole/hr | 12.3028 | 12.3028 | 0.0000 |
| n-Butane | lbmole/hr | 7.5388 | 7.5388 | 0.0000 |
| 1-Butene | lbmole/hr | 13.3741 | 13.3741 | 0.0000 |
| 1-Pentane | lbmole/hr | 4.2007 | 4.2007 | 0.0000 |
| n-Pentane | lbmole/hr | 0.9955 | 0.9955 | 0.0000 |
| 1-Pentene | lbmole/hr | 3.3890 | 3.3890 | 0.0000 |
| n-Hexane | lbmole/hr | 0.5417 | 0.5417 | 0.0000 |
| H2O | lbmole/hr | 0.1203 | 0.1203 | 0.1203 |
| E Glycol | lbmole/hr | 0.0002 | 0.0002 | 0.0002 |

Fig. 3G
Table A

| STREAM/DESCRIPTION | UNIT | 190 | 200 | 210 |
|---|---|---|---|---|
| Vapour Frac |  | 1.0000 | 1.0000 | 0.5805 |
| Temperature | °F | 120.0000 | 120.0000 | -70.0000 |
| Pressure | psia | 800.0001 | 1189.5122 | 1182.0122 |
| Molar Flow | lbmole/hr | 6333.7631 | 6617.4837 | 6617.4837 |
| Mass Flow | lb/hr | 120181.9778 | 121833.8604 | 121833.8604 |
| Liq.Vol.Flow | Barrel/day | 24477.0784 | 25156.3169 | 25156.3169 |
| Enthalpy | Btu/hr | 2.73506E+07 | 2.72362E+07 | 6.81948E+06 |
| Density | lb/ft3 | 2.7053 | 4.0088 | 15.9180 |
| Mole Wt |  | 18.9748 | 18.4109 | 18.4109 |
| Spec. Heat | Btu/lbmole-F | 11.0538 | 11.5801 | 13.4150 |
| Therm Cond. | Btu/hr-ft-F | 0.0264 | 0.0293 | 0.0294 |
| Viscosity | cP | 0.0137 | 0.0146 | 0.0286 |
| Z Factor |  | 0.9020 | 0.8782 | 0.7040 |
| Sur Tension | dyne/cm | --- | --- | --- |
| Std Density | lb/ft3 | --- | --- | --- |
| Hydrogen | lbmole/hr | 760.3160 | 985.4894 | 985.4894 |
| Nitrogen | lbmole/hr | 394.1381 | 398.4535 | 398.4535 |
| CO | lbmole/hr | 26.3160 | 26.8625 | 26.8625 |
| Methane | lbmole/hr | 3599.2311 | 3639.3499 | 3639.3499 |
| Ethylene | lbmole/hr | 373.6366 | 377.8064 | 377.8064 |
| Ethane | lbmole/hr | 1000.7051 | 1008.8472 | 1008.8472 |
| Propene | lbmole/hr | 25.6550 | 25.8609 | 25.8609 |
| Propane | lbmole/hr | 111.4224 | 112.3750 | 112.3750 |
| 1-Butane | lbmole/hr | 12.3028 | 12.3572 | 12.3572 |
| n-Butane | lbmole/hr | 7.5388 | 7.5723 | 7.5723 |
| 1-Butene | lbmole/hr | 13.3741 | 13.3787 | 13.3787 |
| 1-Pentane | lbmole/hr | 4.2007 | 4.2025 | 4.2025 |
| n-Pentane | lbmole/hr | 0.9955 | 0.9959 | 0.9959 |
| 1-Pentene | lbmole/hr | 3.3890 | 3.3904 | 3.3904 |
| n-Hexane | lbmole/hr | 0.5417 | 0.5419 | 0.5419 |
| $H_2O$ | lbmole/hr | 0.0000 | 0.0000 | 0.0000 |
| E Glycol | lbmole/hr | 0.0000 | 0.0000 | 0.0000 |

Fig. 3H
Table A

| STREAM/ DESCRIPTION | UNIT | 220 | 230 | 240 |
|---|---|---|---|---|
| Vapour Frac |  | 1.0000 | 0.0000 | 0.8736 |
| Temperature | °F | -70.0000 | -70.0000 | -133.83 |
| Pressure | psia | 1182.0122 | 1182.0122 | 379.34 |
| Molar Flow | lbmole/hr | 3841.4340 | 2776.0497 | 3841.43 |
| Mass Flow | lb/hr | 59064.9844 | 62768.8545 | 59064.9844 |
| Liq.Vol.Flow | Barrel/day | 12941.9299 | 12214.3835 | 12941.9299 |
| Enthalpy | Btu/hr | 7.85041E+06 | -1.03093E+06 | 6.01583E+06 |
| Density | lb/ft3 | 6.1734 | --- | 2.2043 |
| Mole Wt |  | 15.3758 | 22.6108 | 15.3758 |
| Spec. Heat | Btu/lbmole-F | --- | --- | --- |
| Therm Cond. | Btu/hr-ft-F | --- | --- | --- |
| Viscosity | cP | 1.1738 | --- | 1.2800 |
| Z Factor |  | 0.7040 | --- | 0.8534 |
| Sur Tension | dyne/cm | --- | --- | --- |
| Std Density | lb/ft3 | --- | --- | --- |
| Hydrogen | lbmole/hr | 880.4557 | 104.9346 | 880.4557 |
| Nitrogen | lbmole/hr | 316.1496 | 82.4486 | 316.1496 |
| CO | lbmole/hr | 20.7437 | 6.1073 | 20.7437 |
| Methane | lbmole/hr | 2213.4319 | 1425.7792 | 2213.4319 |
| Ethylene | lbmole/hr | 130.2244 | 247.3460 | 130.2244 |
| Ethane | lbmole/hr | 263.1379 | 745.6470 | 263.1379 |
| Propene | lbmole/hr | 3.4572 | 22.4860 | 3.4572 |
| Propane | lbmole/hr | 11.9084 | 100.4930 | 11.9084 |
| 1-Butane | lbmole/hr | 0.7682 | 11.6594 | 0.7682 |
| n-Butane | lbmole/hr | 0.3335 | 7.2177 | 0.3335 |
| 1-Butene | lbmole/hr | 0.7682 | 12.7698 | 0.7682 |
| 1-Pentane | lbmole/hr | 0.0812 | 4.1640 | 0.0812 |
| n-Pentane | lbmole/hr | 0.0147 | 1.1104 | 0.0147 |
| 1-Pentene | lbmole/hr | 0.0693 | 3.3312 | 0.0693 |
| n-Hexane | lbmole/hr | 0.0030 | 0.5552 | 0.0030 |
| H2O | lbmole/hr | 0.0000 | 0.0000 | 0.0000 |
| E Glycol | lbmole/hr | 0.0000 | 0.0000 | 0.0000 |

Fig. 3I
Table A

| STREAM/ DESCRIPTION | UNIT | 250 | 260 | 270 |
|---|---|---|---|---|
| Vapour Frac | | 0.3527 | 1.0000 | 0.0000 |
| Temperature | °F | -104.1291 | -130.4062 | -105.8555 |
| Pressure | psia | 389.3441 | 375.0000 | 380.0000 |
| Molar Flow | lbmole/hr | 2776.0497 | 4339.3880 | 2278.0956 |
| Mass Flow | lb/hr | 62768.8545 | 63552.0300 | 58281.8132 |
| Liq.Vol.Flow | Barrel/day | 12214.3835 | 14118.7602 | 11037.5533 |
| Enthalpy | Btu/hr | -1.03093E+06 | 9.16383E+06 | -4.17912E+06 |
| Density | lb/ft3 | --- | 1.8436 | --- |
| Mole Wt | | 22.6108 | 14.6455 | 25.5835 |
| Spec. Heat | Btu/lbmole-F | --- | --- | --- |
| Therm Cond. | Btu/hr-ft-F | --- | --- | --- |
| Viscosity | cP | --- | 1.2719 | --- |
| Z Factor | | --- | 0.8431 | --- |
| Sur Tension | dyne/cm | --- | --- | --- |
| Std Density | lb/ft3 | --- | --- | --- |
| Hydrogen | lbmole/hr | 104.9346 | 979.3564 | 6.1326 |
| Nitrogen | lbmole/hr | 82.4486 | 380.7465 | 17.7076 |
| CO | lbmole/hr | 6.1073 | 25.3507 | 1.5126 |
| Methane | lbmole/hr | 1425.7792 | 2741.3215 | 898.0298 |
| Ethylene | lbmole/hr | 247.3460 | 92.6806 | 285.1264 |
| Ethane | lbmole/hr | 745.6470 | 118.7213 | 890.1248 |
| Propene | lbmole/hr | 22.4860 | 0.3341 | 25.5260 |
| Propane | lbmole/hr | 100.4930 | 0.8505 | 111.5241 |
| 1-Butane | lbmole/hr | 11.6594 | 0.0108 | 12.3472 |
| n-Butane | lbmole/hr | 7.2177 | 0.0038 | 7.5678 |
| 1-Butene | lbmole/hr | 12.7698 | 0.0078 | 13.3701 |
| 1-Pentane | lbmole/hr | 4.1640 | 0.0001 | 4.2030 |
| n-Pentane | lbmole/hr | 1.1104 | 0.0000 | 0.9955 |
| 1-Pentene | lbmole/hr | 3.3312 | 0.0001 | 3.3898 |
| n-Hexane | lbmole/hr | 0.5552 | 0.0000 | 0.5421 |
| $H_2O$ | lbmole/hr | 0.0000 | 0.0000 | 0.0000 |
| E Glycol | lbmole/hr | 0.0000 | 0.0000 | 0.0000 |

Fig. 3J
Table A

| STREAM/ DESCRIPTION | UNIT | 280 | 290 | 300 |
|---|---|---|---|---|
| Vapour Frac |  | 0.9515 | 0.1926 | 1.0000 |
| Temperature | °F | -179.7690 | -136.8150 | -172.7854 |
| Pressure | psia | 136.9431 | 146.9431 | 130.0000 |
| Molar Flow | lbmole/hr | 4339.3880 | 2278.0956 | 5217.9071 |
| Mass Flow | lb/hr | 63552.0300 | 58281.8132 | 77139.5740 |
| Liq.Vol.Flow | Barrel/day | 14118.7602 | 11037.5533 | 17209.6276 |
| Enthalpy | Btu/hr | 7.31130E+06 | -4.17912E+06 | 1.04106E+07 |
| Density | lb/ft3 | 0.7630 | --- | 0.6839 |
| Mole Wt |  | 14.6454 | 25.5835 | 14.7596 |
| Spec. Heat | Btu/lbmole-F | --- | --- | 8.2305 |
| Therm Cond. | Btu/hr-ft-F | --- | --- | 0.0145 |
| Viscosity | cP | 1.3247 | --- | 0.0070 |
| Z Factor |  | 0.9180 | --- | 0.9153 |
| Sur Tension | dyne/cm | --- | --- | --- |
| Std Density | lb/ft3 | --- | --- | --- |
| Hydrogen | lbmole/hr | 979.3998 | 6.1508 | 985.4901 |
| Nitrogen | lbmole/hr | 380.5643 | 17.7681 | 398.4537 |
| CO | lbmole/hr | 25.1684 | 1.5946 | 26.8625 |
| Methane | lbmole/hr | 2741.1913 | 898.0252 | 3639.3219 |
| Ethylene | lbmole/hr | 92.8629 | 285.2175 | 95.5578 |
| Ethane | lbmole/hr | 118.8992 | 890.0519 | 72.1624 |
| Propene | lbmole/hr | 0.3359 | 25.5146 | 0.0223 |
| Propane | lbmole/hr | 0.8678 | 111.6266 | 0.0364 |
| 1-Butane | lbmole/hr | 0.0108 | 12.3017 | 0.0001 |
| n-Butane | lbmole/hr | 0.0038 | 7.5177 | 0.0000 |
| 1-Butene | lbmole/hr | 0.0078 | 13.4407 | 0.0000 |
| 1-Pentane | lbmole/hr | 0.0001 | 4.1005 | 0.0000 |
| n-Pentane | lbmole/hr | 0.0000 | 0.9112 | 0.0000 |
| 1-Pentene | lbmole/hr | 0.0001 | 3.4171 | 0.0000 |
| n-Hexane | lbmole/hr | 0.0000 | 0.4556 | 0.0000 |
| $H_2O$ | lbmole/hr | 0.0000 | 0.0000 | 0.0000 |
| E Glycol | lbmole/hr | 0.0000 | 0.0000 | 0.0000 |

Fig. 3K
Table A

| STREAM/DESCRIPTION | UNIT | 310 |
|---|---|---|
| Vapour Frac | | 0.000 |
| Temperature | °F | -30.8026 |
| Pressure | psia | 140.0000 |
| Molar Flow | lbmole/hr | 1399.5765 |
| Mass Flow | lb/hr | 44694.2606 |
| Liq.Vol.Flow | Barrel/day | 7946.6865 |
| Enthalpy | Btu/hr | -2.62294E+06 |
| Density | lb/ft3 | 30.6421 |
| Mole Wt | | 31.9341 |
| Spec. Heat | Btu/lbmole-F | --- |
| Therm Cond. | Btu/hr-ft-F | --- |
| Viscosity | cP | 0.0987 |
| Z Factor | | --- |
| Sur Tension | dyne/cm | --- |
| Std Density | lb/ft3 | 24.1408 |
| Hydrogen | lbmole/hr | 0.0000 |
| Nitrogen | lbmole/hr | 0.0000 |
| CO | lbmole/hr | 0.0000 |
| Methane | lbmole/hr | 0.0282 |
| Ethylene | lbmole/hr | 282.2484 |
| Ethane | lbmole/hr | 936.6840 |
| Propene | lbmole/hr | 25.8386 |
| Propane | lbmole/hr | 112.3385 |
| 1-Butane | lbmole/hr | 12.3571 |
| n-Butane | lbmole/hr | 7.5723 |
| 1-Butene | lbmole/hr | 13.3786 |
| 1-Pentane | lbmole/hr | 4.2025 |
| n-Pentane | lbmole/hr | 0.9959 |
| 1-Pentene | lbmole/hr | 3.3904 |
| n-Hexane | lbmole/hr | 0.5419 |
| $H_2O$ | lbmole/hr | 0.0000 |
| E Glycol | lbmole/hr | 0.0000 |

METHOD AND APPARATUS FOR RECOVERY OF H₂ AND C₂ AND HEAVIER COMPONENTS

BACKGROUND OF THE INVENTION

The present invention relates to a method and apparatus for the improved recovery of hydrogen and ethylene and heavier hydrocarbon components from a hydrocarbon bearing gas such as the off-gas from a refinery.

Hydrocarbon bearing gas contains as components light, often non-hydrocarbon components (e.g. hydrogen, nitrogen, etc.), methane, ethane, and a substantial quantity of hydrocarbons of higher molecular weight, for example, propane, butane, pentane and often their unsaturated analogs. The existing market for hydrogen and ethylene and heavier hydrocarbon components has created a need for a more efficient, safe, and economically sound process that yields a satisfactory level of hydrogen and ethylene and heavier hydrocarbons recovery from a hydrocarbon bearing feed gas.

While production of ethylene by thermal cracking of hydrocarbon feedstocks is expected to remain the dominant route of production, the large capital investment required for world scale ethylene plants has forced ethylene producers and users to explore alternative sources for ethylene. Refineries that operate fluid catalytic cracking (FCC and delayed coker units) generally produce off-gases that contain substantial amounts of ethylene and some propylene. Additionally, these off-gases contain significant quantities of hydrogen, which could be better utilized by the refiner to meet its hydroprocessing demands for hydrogen. In order to take advantage of this source of hydrogen and $C_2$ and heavier components, off-gases from FCC, delayed coker, and other units have been treated utilizing cryogenic separation.

Cryogenic processes typically utilize the principal of gas expansion through a mechanical device to produce power while simultaneously extracting heat, the desirability of such equipment depending upon the pressure of the gas source, the composition of the gas, and the desired end results. In the typical cryogenic expansion-type recovery processes used in the prior art, a gas stream under pressure is cooled by heat exchange with other streams of the process and/or external sources of cooling such as refrigeration systems. As the gas is cooled, liquids are condensed, collected, and separated so as to thereby obtain desired hydrocarbons. Typically the high pressure liquid feed is transferred to a demethanizer column operating at cryogenic temperatures after the pressure is adjusted to the operating pressure of the demethanizer. In such a fractionating column the liquid feed is fractionated to separate the residual methane and lighter components from the desired products of ethylene/ethane and heavier hydrocarbon components. In the ideal operation of such separation processes, the vapors leaving the process contain substantially all of the methane and lighter components found in the feed gas and substantially no $C_2$ and heavier hydrocarbons. The bottom fraction leaving the demethanizer typically contains substantially all of the $C_2$ and heavier hydrocarbon components with very little methane or lighter components.

There are several disadvantages associated with using such cryogenic processes to separate FCC and other off-gases. The primary problem, the formation of $NO$ and $NO_x$ compounds, appears to be more severe with FCC off-gases but is of concern with any off-gas stream. $NO_x$ compounds are typically volatile and hazardous species that concentrate in the coldest part of the cryogenic unit. It is theorized that at low temperatures such as those present during the typical cryogenic processing of off-gases the following reactions occur:

$$2\ NO + O_2 \rightarrow 2\ NO_2$$

$$NO + NO_2 \rightarrow N_2O_3$$

$$N_2O_3 + \text{unsaturated hydrocarbon} \rightarrow NO_x/\text{hydrocarbon gum}$$

Some of the $NO_x$/hydrocarbon gums are stable. However, some, including those involving reaction with butadiene, isoprene and other dienes are known to be quite unstable. Additionally, the reaction $$N_2O_3 + NH_3 \rightarrow NH_4NO_x\ \text{salts}$$

is known to occur at about $-112°$ F. ($-80°$ C.). $NH_4NO_3$ is known to react violently with hydrocarbons at $410°$ F. ($210°$ C.), where it dissociates. Further, $NH_4NO_2$ dissociates at lower temperatures of about $122°$ to $140°$ F. ($50°$ to $60°$ C.) and would be expected to be less stable than the nitrate. The *CRC Handbook of Chemistry and Physics* indicates that $NH_4NO_2$ explodes at its melting point of $140°$ to $158°$ F. ($60°$ to $70°$ C.). These reactions are especially problematic in the cryogenic separation of off-gases because, while some in the industry claim to be capable of testing for $NO_x$, there is no method known to accurately and dependably measure the presence of $NO_x$ at the levels they are present in off-gases, typically around 3 to 25 ppm.

The experiences of several ethylene producers have proven the dangers involved with cryogenic separation of off-gases. For example, there was an emergency shutdown on Feb. 22, 1990, at the Shell Bette 420,000 tonnes/year steamcracker in Southeast France after an explosion inside the cold box. As a result, the plant was out of operation for nearly 5 months, the cold box had to be completely replaced, and a gas cloud estimated at 20 tons of hydrocarbons escaped and covered a large part of the steamcracker. The cold box explosion was attributed to the deflagration of gums present in the low-pressure methane pass, inside one of the fin-plate heat exchangers of a twin pair. The gums were determined to contain 14 to 21 percent of nitrogen with numerous nitro and nitroso components on short hydrocarbon chains. The source of the $NO_x$ was identified as $NO_x$ components present in the catalytic cracker dry gas that had been part of the Berre steam cracker feed since 1982. Shell reports concluded that the explosion was a deflagration type with a most probable equivalent mass of TNT between 17 and 28 kg (37.4 and 61.6 lb.) However, some local detonations could also have taken place and the presence of perlite had a very important damping effect during the explosion.

The Shell Berre experience and the subsequent determination by others in the industry that NOx compounds were accumulating in the cryogenic portions of ethylene plants have been well documented as a result of a study by the Industrial Task Group on Nitrogen Oxides in Ethylene Plants, sponsored by the AIChE Center for Chemical Process Safety. For example, Union Carbide reported the discovery of what was roughly estimated to be 100 pounds of $N_2O_3$ accumulation in the cold section of the Union Carbide Texas City, Texas Olefins plant. That study further showed that pyrolizing cat cracker dry gas does not remove sufficient NO to prevent $NO_x$ compounds from forming and accumulating in the cryogenic section of an ethylene plant. Further, amine and/or caustic washing also proved to be inadequate to remove $NO_x$ from cat cracker dry gas or cracked gas.

While there are many variations in how technical choices currently available in the industry can be implemented to recover the valuable components of off-gases, there are about five primary processes for recovery of hydrogen or $C_2$ and heavier hydrocarbons from off-gases that have been developed or adapted in an attempt to address the various problems associated with cryogenic separation, including the formation of NOx compounds in the cold sections. It has been suggested that eliminating at least one of the four essential ingredients for the formation of $NO_x$ gums and ammonium nitrate—oxygen, NO, unsaturated hydrocarbons and cryogenic temperatures—may help the problem.

As noted in the AIChE Ethylene Producers Committee, Task Group on Nitrogen Oxides in Cryogenic Sections of Ethylene Plants in the paper "Potential Hazards of Nitrogen Oxide Compound Accumulations in Cryogenic Ethylene Recovery Facilities", presented at the Fifth Annual Ethylene Producers Conference, AIChE Spring Meet on Mar. 30, 1993, some operators are demethanizing refinery gases prior to feeding the bottom stream from the demethanizer to the ethylene recovery unit, theorizing that the NO should tend to go with the overheads in the refinery demethanization step so that the probability of mingling accumulated $NO_x$ with reactive diolefins would be lowered. However, the Task Group concluded that the lack of an adequate analytical method for determining the amount of NO and $NO_x$ compounds in a given stream and a real question concerning whether $NO_x$ compounds really go with the overheads causes concern regarding the safety of this process. Further, the overheads that are created as residual gas contain substantial amounts of $C_2$ that are not recovered in this scheme.

Brown & Root Braun's Refinery Off-Gas Enrichment process is similar to a standard cryogenic ethylene plant. This process gathers the available off-gases and sorts them into two groups, one containing nitrogen and olefins (typically FCC unit tail gas) and a second group containing minimal nitrogen and minimal olefins (typically hydrotreater, catalytic reformer, crude unit and ethylene plant off-gases). The two groups are then processed separately but in similar fashion, having acid gases removed in an amine unit, being compressed, dried by molecular sieves and then stage-cooled in parallel passes of the heat exchange system within the cryogenic section. The condensate fractions may be combined or kept separate, depending upon the end uses of the recovered materials and as dictated by the need to generate refrigeration. A demethanizer may be used in the cryogenic section to provide a sharp separation between rejected methane and recovered $C_2$ and heavier hydrocarbons. If the condensate fractions are kept separate, two demethanizers may be utilized in parallel, one for each condensate fraction. However, while this approach minimizes the likelihood of formation of NOx compounds in the cryogenic section of the train processing the second group of gases which initially contained minimal nitrogen and minimal olefins, it does nothing to minimize or prevent the formation of NOx compounds in the cryogenic section of the train processing the first group of gases which initially contained nitrogen and olefins. Therefore, this scheme of processing high-risk and low-risk gases in parallel does not adequately address the goal of preventing the dangerous NOx compounds from forming. Further, it exposes the low-risk gas processing streams to the risk of disruption should a problem arise as a result of processing the high-risk gases.

Stone & Webster Engineering Corporation and Air Products a Chemicals, Inc. have developed what they term an Advanced Recovery System ("ARS") to separate methane from the ethylene-ethane fraction of off-gases. The ARS process utilizes self-refluxing plate fin exchangers, also called dephlegmators, in the cryogenics section of the system. Dephlegmators can achieve simultaneous heat and mass transfer and serve the function of a rectification column and condenser. The dephlegmators used in the ARS typically provide 10 to 15 stages of fractionation to partially separate the methane and lighter components from the $C_2$ and heavier components while chilling and partially condensing the heavier fractions of the inlet gas stream. As the feed is cooled and condensed, liquid runs back to recontact the incoming gas. This liquid reflux through the dephlegmators makes the dephlegmators self-washing. While recognizing the potential hazard from the presence of $NO_x$ compounds at cryogenic temperatures, the ARS system uses the self-flushing nature of the dephlegmators to minimize accumulations of heavy ends, tends to eliminate dead ends within exchangers where NOx compounds tend to form, minimizes the dienes entering the cold sections, and allows more frequent shutdown, solvent washing, and inspection to minimize accumulations of $NO_x$ compounds.

Lummus Crest has designed what they call a Low-Pressure Recovery (LPR) system. In the LPR system, the treated feed gas is initially processed with a front-end deethanization or depropanization unit upstream of the cryogenic section of the recovery unit followed by a feed chilling and demethanization unit to produce what is believed to be a relatively $NO_x$ free ethylene-ethane stream. However, by treating the overhead gas from the demethanization unit as a residual gas, substantial amounts of $C_2$ are not recovered, making this system of questionable economic benefit in the current market. Further, the lack of an adequate analytical method for determining the amount of NO and $NO_x$ compounds in a given stream and a real question concerning whether $NO_x$ compounds really go with the overheads causes concern regarding the safety of this process.

Kinetics Technology International Corporation (KTI) and Advanced Extraction Technologies, Inc. (AET) have employed a refrigerated lean oil extraction process described in a family of U.S. patents originating with Ser. No. 374,270, filed May 3, 1982, including U.S. Pat. No. 5,019,143, issued May 28, 1991 (the "Mehra process") to, at least in theory, recover ethylene without the use of cryogenics or high pressures. While this method may work at some level of $C_2$ recovery, the materials costs involved, i.e. lean oil, increases the cost of recovery compared to cryogenic systems. Thus, not only are the capital investment costs higher in the Mehra process, operating costs are as well. Further, although the Mehra process has operated successfully in a nitrogen rejection process, it has not been proven in the present application. Additionally, during the hydrocarbon recovery portion of the Mehra process, methane and heavier hydrocarbons are removed from the feed gas, but the inerts remain in the $H_2$-rich stream. This inherently causes a lower and non-controllable level of $H_2$ purity, requiring a secondary purification step for the $H_2$-rich stream, the most common of which would likely be a costly pressure swing adsorption process.

SUMMARY OF THE INVENTION

The present invention relates to a process and apparatus for separating a hydrocarbon gas into a fraction containing a predominant portion of hydrogen, a fraction containing a predominant portion of methane, and a fraction containing a predominant portion of $C_2$ and heavier components in which process the feed gas is treated in a three phase gas/hydrocarbon/glycol-water separator wherein the refrigerated feed gas is separated into a water-glycol solution (products of glycol dehydration), a hydrocarbon-rich liquid and a $H_2$-rich vapor; wherein the vapor is directed into a $H_2$ membrane separator to produce a second, substantially $H_2$ vapor and a first hydrocarbon-rich vapor; the liquid is directed to a first demethanizer to produce a second liquid comprised substantially of $C_2$ and heavier components and a second hydrocarbon-rich vapor containing substantially no dienes; the hydrocarbon-rich vapors are directed to a dehydrator, cooled, directed to an absorber and a second demethanizer, whereby the hydrocarbon-rich vapors are separated into a fraction containing a predominant portion of the methane and a fraction comprised substantially of $C_2$ and heavier components. The foregoing process and apparatus provides for utilization of cryogenic separation of methane from $C_2$ and heavier components while minimizing the likelihood of introduction of dienes associated with the formation of $NO_x$ compounds, including $NO_x$ gums and "blue ice" in the sections of the apparatus operating at cryogenic temperatures.

In the present invention, an inlet hydrocarbon gas stream is separated into a fraction containing a predominant portion of hydrogen, a fraction containing a predominant portion of the methane, and a fraction containing a predominant portion of the $C_2$ and heavier components, preferably in a three phase gas/glycol separator. In the gas/glycol separator, the feed gas is separated into a liquid comprised primarily of water and glycol, a first hydrocarbon-rich liquid and a $H_2$-rich vapor. The $H_2$-rich vapor is directed into a $H_2$ membrane separator to produce a second, substantially $H_2$ vapor and a first hydrocarbon-rich vapor. The first hydrocarbon-rich liquid from the gas/glycol separator is separated by a first demethanizer into a second liquid comprised substantially of $C_2$ and heavier components and a second hydrocarbon-rich vapor containing substantially no dienes.

The second liquid is directed to any of many standard processing units designed to process liquid streams comprised substantially of C2 and heavier components with substantially no lighter components. Such units frequently include a deethanization unit which splits the stream into a $C_2$ stream and a stream containing $C_3$ and heavier components. The $C_2$ stream is commonly subjected to arsine removal and acetylene conversion and then split by an ethane/ethylene splitter unit into ethylene and ethane products. The stream containing $C_3$ and heavier components is typically processed in a depropanization unit to produce a $C_3$ product stream and a stream containing $C_4$ and heavier components which are returned to the plant for further processing.

The first and second hydrocarbon-rich vapors from the $H_2$ membrane separator and the first demethanizer respectively are directed to a molecular sieve dehydrator where any remaining water, glycol and traces of sulfur compounds are removed. The hydrocarbon-rich vapors are then cooled to provide a third vapor fraction and a third liquid fraction. These third vapor and liquid fractions are directed to an absorber and a second demethanizer, unlike the first demethanizer, which, operates at cryogenic temperatures. The second demethanizer separates the third vapor and liquid fractions into a fourth vapor fraction containing a predominant portion of the methane and a fourth liquid fraction comprised substantially of $C_2$ and heavier components. The fourth liquid fraction is directed to any of many standard processing units designed to process liquid streams comprised substantially of C2 and heavier components with substantially no lighter components, as described above. The fourth vapor fraction may be utilized as a methane-rich stream or as a residual gas stream.

In this manner, a higher proportion of the hydrogen and the C2 and heavier hydrocarbon components are recovered.

The foregoing process and apparatus also provides for utilization of cryogenic separation of methane from $C_2$ and heavier components while minimizing the likelihood of introduction of dienes associated with the formation of $NO_x$ compounds, including $NO_x$ gums and "blue ice" in the sections of the apparatus operating at cryogenic temperatures. Thus, the present invention provides a method and apparatus for recovering hydrogen and $C_2$ and heavier components from hydrocarbon gases, including those that contain oxygen, NO and unsaturated hydrocarbons Further, prior to the cryogenic section the straight refrigeration plant produces a hydrogen enriched stream from the 3-phase separator and the first demethanizer produces a liquid stream containing substantial portions of the C2 and heavier components as well as a vapor stream containing substantially less hydrogen than the feed gas. The resulting decrease in volume of the gas stream that must be cooled to cryogenic temperatures decreases substantially the cryogenic plant size and the resulting cooling costs. Furthermore, the hydrogen enriched gas stream when fed to a membrane unit increases the corresponding recovery of hydrogen for any specified hydrogen purity.

Further, since $H_2$ does not respond in the same manner as hydrocarbons under the Joules-Thompson effect, the removal of the $H_2$ prior to cooling aids in the refrigeration of the remaining gas that is cooled to cryogenic temperatures by expansion.

Further, the removal of the $H_2$ and the heavier hydrocarbons prior to cooling makes the cooling of the hydrocarbons via expansion sufficiently efficient that the need for supplemental refrigeration in the cryogenics section is eliminated.

Further, since lean gas responds more favorably to expansion refrigeration than less lean gas and the gas feed to the cryogenic portion of the system is leaner than the gas feed to the cryogenic portion of a conventional system, the expansion refrigeration used to reach cryogenic temperatures is more efficient.

Further, because substantial portions of the $H_2$ and the C2 and heavier components are removed in the pre-cryogenic section of the system where carbon steel construction is sufficient, the cryogenic section, which requires relatively expensive alloy construction (stainless steel and/or aluminum), can be smaller. Therefore, the capital cost of the system is reduced relative to a conventional system.

DESCRIPTION OF THE DRAWINGS

FIG. 3 is a table setting forth physical characteristics of the streams in one preferred embodiment of the invention.

DETAILED DESCRIPTION

Figure 1A:
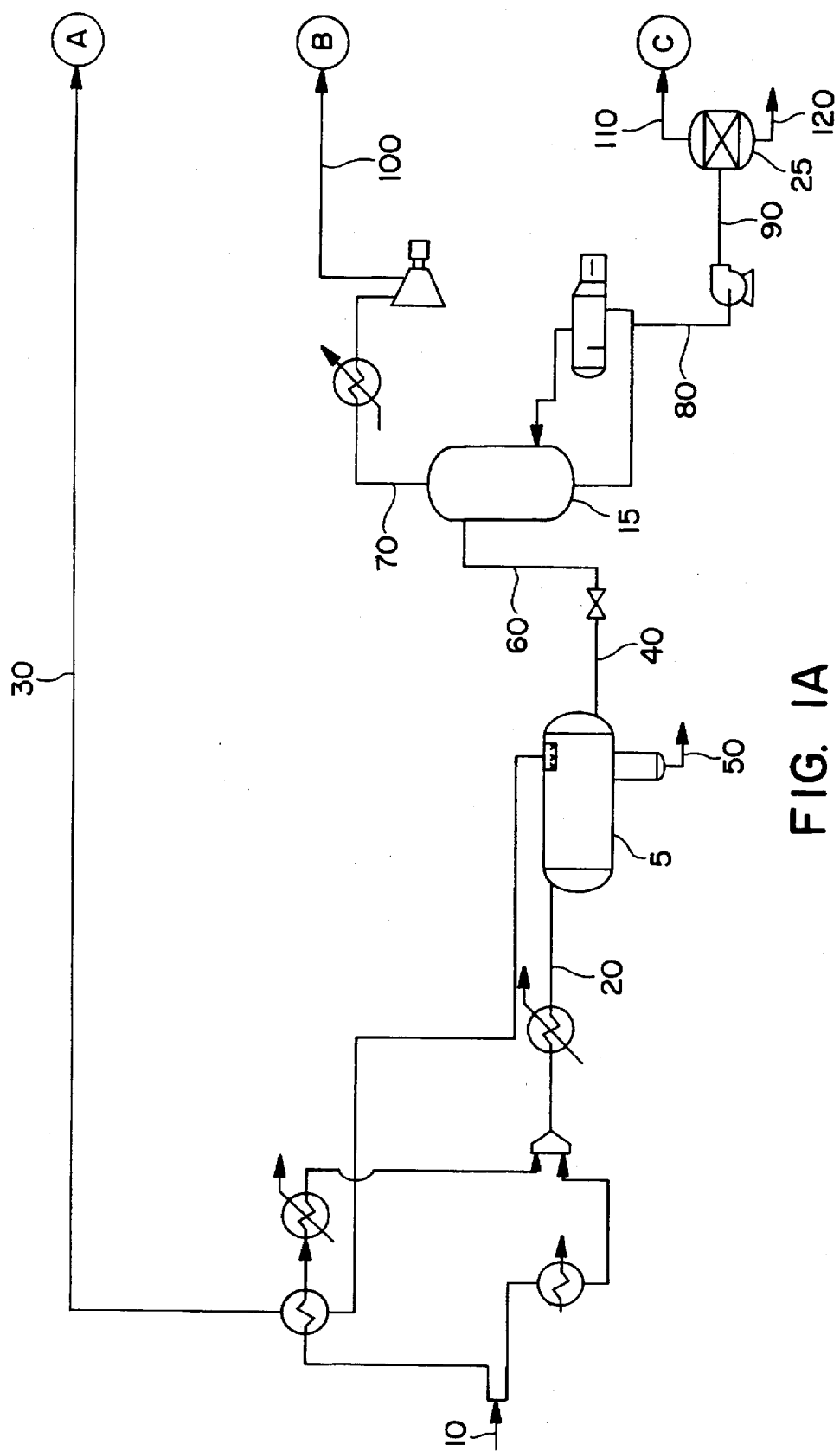
FIG. 1 is a schematic flow diagram illustrating a method of practicing a preferred embodiment of the invention.
Figure 1B:
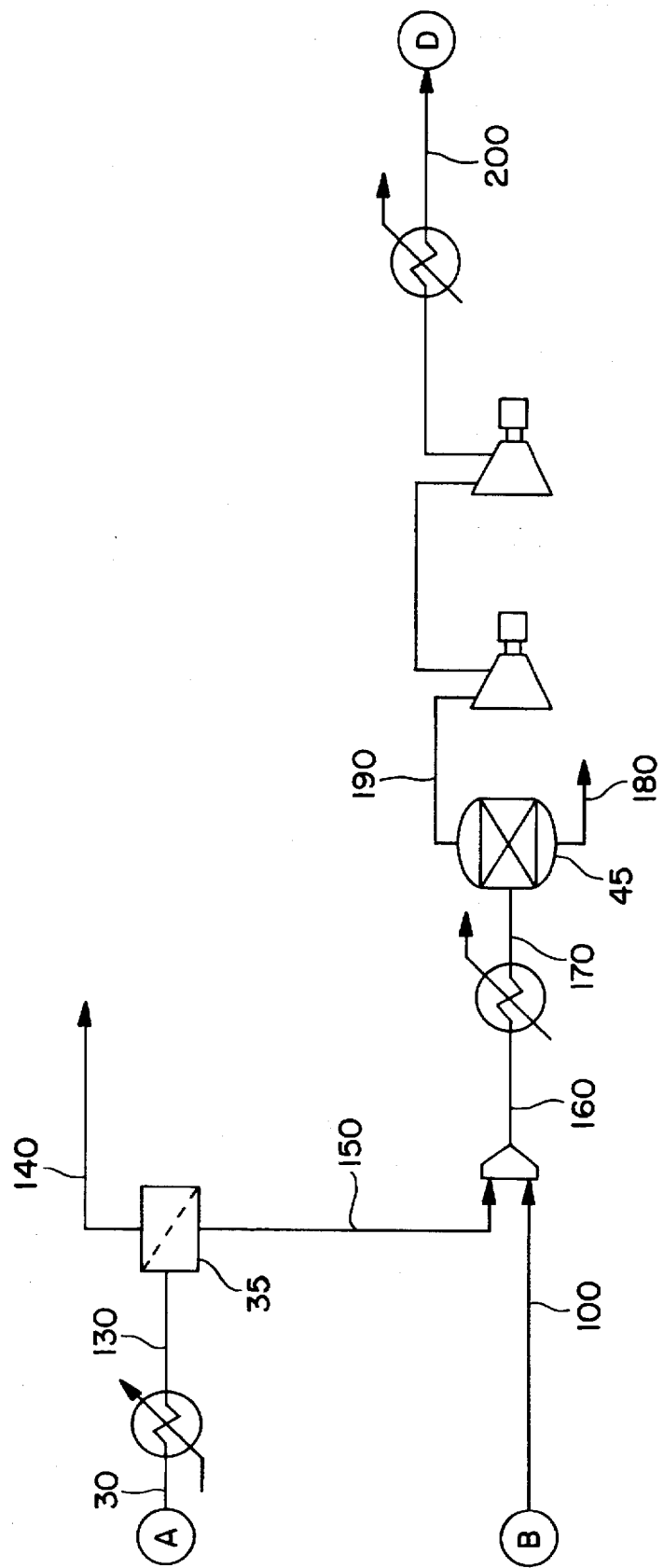
Figure 2:
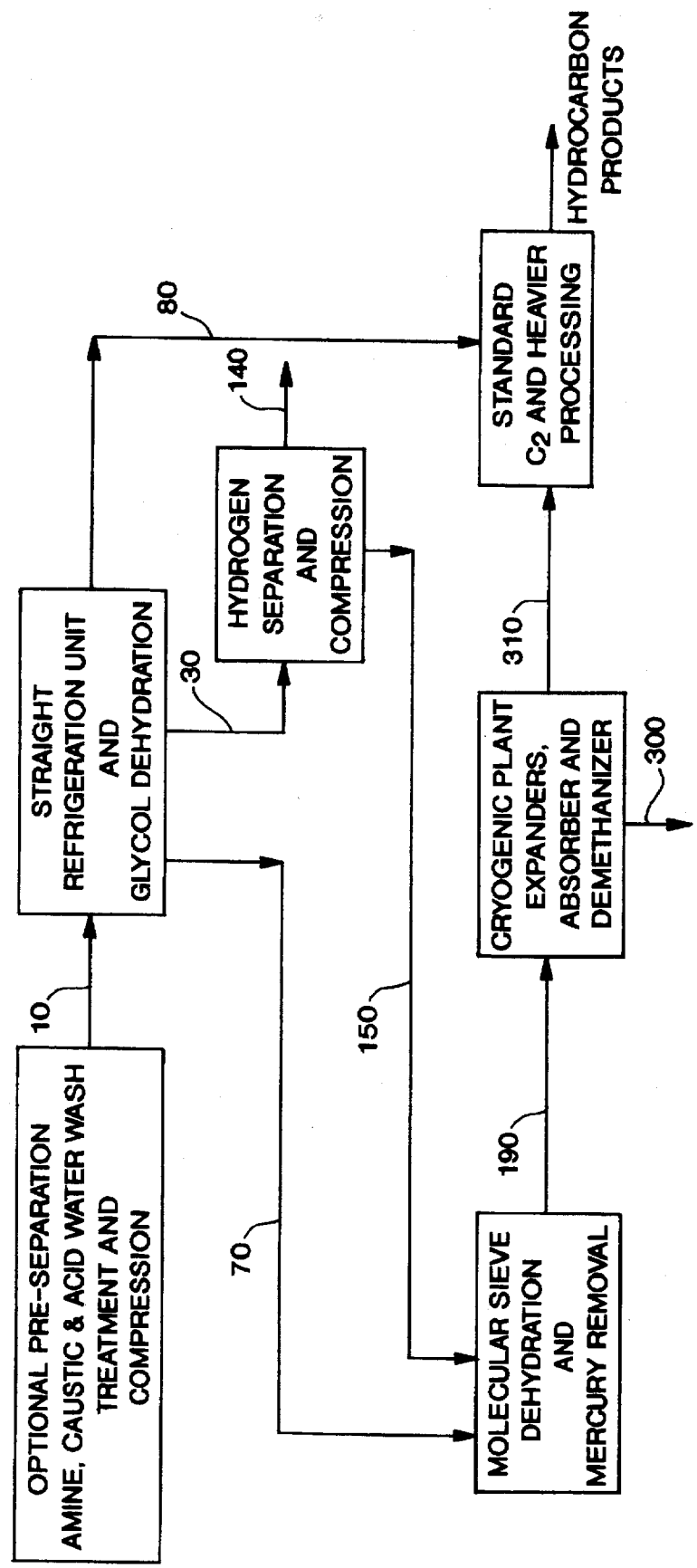
FIG. 2 is a block flow diagram illustrating a method of practicing a preferred embodiment of the invention.

As shown in FIG. 1, an inlet hydrocarbon gas stream 10, typically a refinery offgas stream, is initially provided. The inlet hydrocarbon gas stream 10, if it has not already been so treated, should be treated with an amine treater, caustic treating and acid water wash to remove $CO_2$, $H_2S$, HCN, and $NH_3$, and compressed. The inlet stream 10 is cooled to form stream 20 and enters a separator 5 in which stream 20 is separated into a hydrogen-rich vapor stream 30 and a hydrocarbon-rich liquid stream 40. Preferably, separator 5 is a gas/glycol three phase separator. In this embodiment, a primarily $H_2O$ and glycol liquid stream 50 (which is routed to a glycol degenerator for reuse) is provided in addition to stream 30 and 40. The hydrogen-rich vapor stream 30 passes through a membrane separator 35 to produce a high-purity $H_2$ product stream 140 and a hydrocarbon-rich vapor stream 150.

The hydrocarbon-rich liquid stream 40 is expanded to form a partially vapor, partially liquid hydrocarbon-rich stream 60, which is fed to a first demethanizer (stabilizer) 15. Demethanizer 15 divides stream 60 into a methane-rich vapor stream 70 and a substantially $C_2$ and heavier component liquid stream 80. Stream 80 would typically be dehydrated by dehydrator 25 to remove substantially $H_2O$ stream 120 and form dehydrated stream 110 prior to further processing. Stream 110 could be joined with stream 310, described below, for further processing. Streams 80, 110 or 310 or the combined streams 110 and 310 may be fed directly to a standard process for $C_2$ and heavier components, typically a deethanizer unit which will split stream 80 into a $C_2$ rich stream valuable for treatment by arsine removal and acetylene conversion followed by ethane/ethylene splitting to produce ethane product and ethylene product streams, and a $C_3$ and heavier component stream which would commonly be treated with a depropanizer unit to produce a $C_3$ product stream and a $C_4$ and heavier component stream which would be recycled for further use by the plant.

Methane-rich vapor stream 70 is compressed to form stream 100, which is then combined with hydrocarbon-rich vapor stream 150 to form hydrocarbon-rich vapor stream 160. Stream 160 is cooled to form stream 170 and dehydrated by dehydrator 45, which separates primarily $H_2O$ stream 180 from stream 170 to form stream 190. Dehydrator 45 is preferably a molecular sieve dehydrator. Stream 190 is further compressed to form a high pressure, hydrocarbon-rich vapor stream 200.

Stream 200 serves as the feed stream to the cryogenics section of the process. Stream 200 is chilled and slightly expanded to create a partially vapor, partially liquid stream 210. Stream 210 is fed to high pressure suction scrubber 55 which separates the vapor and liquid fractions of stream 210 into a high-pressure, hydrocarbon-rich vapor stream 220 and a high-pressure, hydrocarbon-rich liquid stream 230. Stream 220 is chilled via expansion to form a partially vapor, partially liquid stream 240. Stream 230 is chilled via expansion to form a partially vapor, partially liquid stream 250.

Streams 240 and 250 serve as feed streams for absorber 65. The vapors exit absorber 65 as vapor stream 260 and are further chilled via expansion to form partially vapor, partially liquid stream 280. The liquids exit absorber 65 as liquid stream 270 and are further chilled via expansion to form partially vapor, partially liquid stream 290.

Streams 280 and 290 serve as feed streams for demethanizer 75. Demethanizer 75 operates at cryogenic temperatures to strip the methane and lighter components from the feed streams 280 and 290 to provide a substantially methane and lighter component stream 300 and a substantially $C_2$ and heavier component liquid stream 310. Stream 300 is typically characterized as residue gas and contains the gases remaining after the desirable $C_2$ and heavier hydrocarbons are recovered.

Stream 310 may be fed along with stream 80 or stream 110, originating from the pre-cryogenic demethanizer 15, directly to a standard process for $C_2$ and heavier components, typically a deethanizer unit which will split stream 80 into a $C_2$ rich stream valuable for treatment by arsine removal and acetylene conversion followed by ethane/ethylene splitting to produce ethane product and ethylene product streams, and a $C_3$ and heavier component stream which would commonly be treated with a depropanizer unit to produce a $C_3$ product stream and a $C_4$ and heavier component stream which would be recycled for further use by the plant.

By way of example and not by way of limitation, the above described method may be utilized on a feed gas 10 with the composition and characteristics shown in Table A, set forth in FIG. 3. In one such embodiment, the composition and characteristics of the various streams resulting from use of the invention are shown in Table A.

In the preferred embodiment noted above, the equipment used to accomplish the method of separating a hydrocarbon gas into a fraction containing a predominant portions of hydrogen, a fraction containing a predominant portion of the methane, and a fraction containing a predominant portion of the $C_2$ and heavier components resulting in the streams in Table A (FIG. 3), are described as follows. The preferred pre-cryogenic multi-stage demethanizer 15 for the given feed parameters is a 20 stage demethanizer (a reboiled fractionator) with the feed and vapor draw at stage 1 (the uppermost stage), the liquid draw and 10.335 MMBtu/hr. imparted to stage 20, and the pressures, temperatures and flowrates at any given stage as shown in Table B:

TABLE B

| Stage No. | Press Psia | Temp. °F. | Flow Rates Liquid | (lb moles/hr) Vapour |
|---|---|---|---|---|
| 1 | 450.0 | −12.5 | 2834.5 | |
| 2 | 450.5 | −7.0 | 2939.7 | 703.1 |
| 3 | 451.1 | −2.4 | 2987.6 | 808.3 |
| 4 | 451.6 | 5.7 | 3064.5 | 856.2 |
| 5 | 452.1 | 19.5 | 3211.8 | 933.2 |
| 6 | 452.6 | 37.1 | 3439.5 | 1080.4 |
| 7 | 453.2 | 53.5 | 3697.9 | 1308.1 |
| 8 | 453.7 | 65.2 | 3916.0 | 1566.5 |
| 9 | 454.2 | 72.2 | 4065.0 | 1784.7 |
| 10 | 454.7 | 76.2 | 4155.1 | 1933.6 |
| 11 | 455.3 | 78.5 | 4207.1 | 2023.8 |
| 12 | 455.8 | 79.8 | 4237.4 | 2075.7 |
| 13 | 456.3 | 80.7 | 4256.2 | 2106.0 |
| 14 | 456.8 | 81.5 | 4269.3 | 2124.8 |
| 15 | 457.4 | 82.3 | 4279.3 | 2137.9 |
| 16 | 457.9 | 83.3 | 4286.0 | 2147.9 |
| 17 | 458.4 | 85.1 | 4283.6 | 2154.6 |
| 18 | 458.9 | 88.9 | 4246.7 | 2152.2 |
| 19 | 459.5 | 98.7 | 4081.0 | 2115.3 |
| 20 | 460.0 | 130.1 | | 1949.6 |

The preferred membrane separator 35 for the given parameters operates with feedstream 130, described in Table A (FIG. 3) above, to produce permeate stream 140 and non-permeate stream 150 described in Table A (FIG. 3). During such operation, membrane separator 35 would also produce 448,112.93 Btu/hr.

The preferred multi-stage absorber 65 is ideally an 8 stage column with feed stream 240, described in Table A (FIG. 3), entering on stage 1 and feedstream 250, described in Table A (FIG. 3), entering on stage 8. Overhead stream 260 leaves stage 1 and bottoms stream 270 leaves stage 8. The pressures, temperatures and flowrates at any given stage are shown in Table C.

TABLE C

| Stage No. | Press Psia | Temp. °F. | Flow Rates Liquid | (lb moles/hr) Vapour |
|---|---|---|---|---|
| 1 | 375.0 | −130.4 | 494.9 | |
| 2 | 375.7 | −117.5 | 523.1 | 992.9 |
| 3 | 376.4 | −115.2 | 519.6 | 1021.0 |
| 4 | 377.1 | −113.4 | 515.1 | 1017.5 |
| 5 | 377.9 | −111.9 | 511.1 | 1013.1 |
| 6 | 378.6 | −110.5 | 507.2 | 1009.1 |
| 7 | 379.3 | −109.0 | 497.6 | 1005.1 |
| 8 | 380.0 | −105.9 | | 995.6 |

The preferred cryogenic multi-stage demethanizer 75 for the given feed parameters is ideally a 15 stage demethanizer with feedstream 280 entering on stage 1, feedstream 290 entering on stage 4, overhead stream 300 leaving stage 1, bottoms stream 310 leaving stage 15, and a side reboiler leaving stage 10 and reentering on stage 9. For the given flowrates, preferably 1.000 MMBtu/hr. are imparted by the side reboiler and 3.655 MMBtu/hr. are imparted to stage 15. The pressures, temperatures and flowrate at any given stage are shown in Table D.

TABLE D

| Stage No. | Press Psia | Temp. °F. | Flow Rates Liquid | (lb moles/hr) Vapour |
|---|---|---|---|---|
| 1 | 130.0 | −172.8 | 214.3 | |
| 2 | 130.7 | −147.6 | 212.3 | 1092.8 |
| 3 | 131.4 | −142.7 | 202.5 | 1090.8 |
| 4 | 132.1 | −138.3 | 2005.6 | 1081.0 |
| 5 | 132.9 | −131.0 | 2001.9 | 606.1 |
| 6 | 133.6 | −113.3 | 2007.7 | 602.3 |
| 7 | 134.3 | −83.7 | 2082.8 | 608.1 |
| 8 | 135.0 | −58.3 | 2189.0 | 683.2 |
| 9 | 135.7 | −45.6 | 2252.8 | 789.4 |
| 10 | 136.4 | −39.9 | 2087.0 | 853.2 |
| 11 | 137.1 | −38.2 | 2096.5 | 687.5 |
| 12 | 137.9 | −37.3 | 2101.2 | 696.9 |
| 13 | 138.6 | −36.5 | 2103.4 | 701.6 |
| 14 | 139.3 | −35.2 | 2099.1 | 703.8 |
| 15 | 140.0 | −30.8 | | 699.6 |

Although a preferred embodiment of the invention has been described, it will be appreciated by those skilled in the art to which the present invention pertains that modifications, changes, and improvements may be made without departing from the spirit of the invention defined by the claims. For example, without limitation as to other modification, changes, and improvements it may be desirable to vary which streams are coupled for heat exchange purposes, vary the purity requirements of the product streams, vary the efficiencies of the intermediary separations, or accomplish the necessary compression and chilling in either more or fewer steps than depicted and described above, depending upon economic and other considerations. Further, it may be desirable to design the apparatus to accomplish the method with a wide variety of feed streams that may deviate substantially in composition and volume from that in the example provided.

What is claimed:

1. A method of separating a hydrocarbon gas into a fraction containing a predominant portion of hydrogen, a fraction containing a predominant portion of the $C_2$ and heavier components, and a fraction containing the residual components comprising:

(a) separating the feed gas into a first hydrocarbon-rich liquid and a $H_2$-rich vapor;

(b) separating the $H_2$-rich vapor into a second, substantially $H_2$ vapor and a first hydrocarbon-rich vapor;

(c) separating at temperatures above −30.8° F. the first hydrocarbon-rich liquid into a second hydrocarbon-rich liquid comprised substantially of $C_2$ and heavier components and a second hydrocarbon-rich vapor;

(d) compressing the first and second hydrocarbon-rich vapors to produce a third hydrocarbon-rich vapor and a third hydrocarbon-rich liquid; and (e) separating at or below −30.8° F. the third hydrocarbon-rich vapor and the third hydrocarbon-rich liquid into a fourth liquid comprised substantially of $C_2$ and heavier components and a fourth vapor containing a predominant portion of methane.

2. The method of claim 1, wherein:

the separation of the first hydrocarbon-rich liquid into a second hydrocarbon-rich liquid comprised substantially of $C_2$ and heavier components and a second hydrocarbon-rich vapor is accomplished at pressures above those found in the cryogenic portions of ethylene plants.

3. The method of claim 1, wherein:

the separation of the third hydrocarbon-rich vapor and the third hydrocarbon-rich liquid into a fourth vapor containing a predominant portion of the methane and a fourth liquid comprised substantially of $C_2$ and heavier components is accomplished at pressures found in the cryogenic portions of ethylene plants.

4. A method of separating a hydrocarbon gas into a fraction containing a predominant portion of hydrogen, a fraction containing a predominant portion of the $C_2$ and heavier components and a fraction containing the residual components comprising:

(a) separating the feed gas into a first hydrocarbon-rich liquid and a $H_2$-rich vapor;

(b) separating the $H_2$-rich vapor into a second, substantially $H_2$ vapor and a first hydrocarbon-rich vapor;

(c) separating at temperatures above −30.8° F. the first hydrocarbon-rich liquid into a second hydrocarbon-rich liquid comprised substantially of $C_2$ and heavier components and a second hydrocarbon-rich vapor;

(d) compressing the first and second hydrocarbon-rich vapors to produce a partially liquid hydrocarbon-rich stream; and (e) separating at or below −30.8° F. the partially liquid hydrocarbon-rich stream into a third liquid comprised substantially of $C_2$ and heavier components and a third vapor containing the residual components from the partially liquid hydrocarbon-rich stream.

5. A method of separating a hydrocarbon gas into a fraction containing a predominant portion of hydrogen, a fraction containing a predominant portion of the $C_2$ and heavier components and a fraction containing the residual components comprising:

(a) separating the feed gas into a first hydrocarbon-rich liquid and a $H_2$-rich vapor;

(b) separating the $H_2$-rich vapor into a second, substantially $H_2$ vapor and a first hydrocarbon-rich vapor;

(c) separating at temperatures above −30.8° F. the first hydrocarbon-rich liquid into a second hydrocarbon-rich liquid comprised substantially of $C_2$ and heavier components and a second hydrocarbon-rich vapor;

(d) compressing the first and second hydrocarbon-rich vapors to produce a partially liquid hydrocarbon-rich stream; and (e) separating the partially liquid hydrocarbon-rich stream into a third liquid comprised substantially of $C_2$ and heavier components and a third vapor containing substantially all of the methane and lighter components in the partially liquid hydrocarbon-rich stream.

6. A method of separating a hydrocarbon gas into a fraction containing a predominant portion of hydrogen, a fraction containing a predominant portion of the $C_2$ and heavier components and a fraction containing the residual components comprising:

(a) separating the feed gas into a first hydrocarbon-rich liquid and a $H_2$-rich vapor;

(b) separating the $H_2$-rich vapor into a second, substantially $H_2$ vapor and a first hydrocarbon-rich vapor;

(c) separating at temperatures above $-30.8°$ F. the first hydrocarbon-rich liquid into a second hydrocarbon-rich liquid comprised substantially of $C_2$ and heavier components and a second hydrocarbon-rich vapor;

(d) compressing the first and second hydrocarbon-rich vapors to produce a partially liquid hydrocarbon-rich stream; and (e) separating at or below $-30.8°$ F. the partially liquid hydrocarbon-rich stream into a third liquid comprised substantially of $C_2$ and heavier components and a third vapor containing substantially all of the components from the partially liquid hydrocarbon-rich stream that are lighter than $C_2$.

7. A method of separating a hydrocarbon gas into a fraction containing a predominant portion of hydrogen, a fraction containing a predominant portion of the $C_2$ and heavier components and a fraction containing the residual components comprising:

(a) separating the feed gas into a first hydrocarbon-rich liquid and a $H_2$-rich vapor;

(b) separating the $H_2$-rich vapor into a second, substantially $H_2$ vapor and a first hydrocarbon-rich vapor;

(c) separating at temperatures above $-30.8°$ F. the first hydrocarbon-rich liquid into a second hydrocarbon-rich liquid comprised substantially of $C_2$ and heavier components and a second hydrocarbon-rich vapor;

(d) compressing the first and second hydrocarbon-rich vapors to produce a partially liquid hydrocarbon-rich stream; and (e) separating at or below $-30.8°$ F. the partially liquid hydrocarbon-rich stream into a third liquid comprised substantially of $C_2$ and heavier components and a third vapor containing the remainder of the components from the partially liquid hydrocarbon-rich stream.

8. A method of separating a hydrocarbon gas into a fraction containing a predominant portion of hydrogen, a fraction containing a predominant portion of the $C_2$ and heavier components and a fraction containing the residual components comprising:

(a) separating the feed gas into a solid comprised primarily of water and glycol, a first hydrocarbon-rich liquid and a $H_2$-rich vapor;

(b) separating the $H_2$-rich vapor into a second, substantially $H_2$ vapor and a first hydrocarbon-rich vapor;

(c) separating at temperatures above $-30.8°$ F. the first hydrocarbon-rich liquid into a second hydrocarbon-rich liquid comprised substantially of $C_2$ and heavier components and a second hydrocarbon-rich vapor;

(d) dehydrating and cooling the first and second hydrocarbon-rich vapors to produce a third hydrocarbon-rich vapor and a third hydrocarbon-rich liquid;

(e) separating at or below $-30.8°$ F. the third hydrocarbon-rich vapor and the third hydrocarbon-rich liquid into a fourth liquid comprised substantially of $C_2$ and heavier components and a fourth vapor containing a predominant portion of the methane and lighter components.

9. A method of recovering a predominant portion of the $C_2$ and heavier components in a feed gas comprising:

(a) demethanizing the feed gas at temperatures above $-30.8°$ F. to produce a substantially $C_2$ and heavier component stream and a methane and lighter component-rich stream;

(b) demethanizing the methane and lighter component-rich stream at or below $-30.8°$ F. to produce a second substantially $C_2$ and heavier component stream and a residue stream.

10. The method of claim 9 wherein:

the residue stream is substantially all of the methane and lighter components from the feed gas.

11. A method of separating a hydrocarbon gas into a fraction containing a predominant portion of hydrogen, a fraction containing a predominant portion of the $C_2$ and heavier components and a fraction containing the residual components comprising:

(a) separating the feed gas into a first hydrocarbon-rich liquid and a $H_2$-rich vapor;

(b) separating the $H_2$-rich vapor into a second, substantially $H_2$ vapor and a first hydrocarbon-rich vapor;

(c) demethanizing the first hydrocarbon-rich liquid at temperatures above $-30.8°$ F. to produce a substantially $C_2$ and heavier component stream and a methane and lighter component-rich stream;

(d) demethanizing the methane and lighter component-rich stream and the first hydrocarbon-rich vapor at or below $-30.8°$ F. to produce a second substantially $C_2$ and heavier component stream and a residue stream.

12. The method of claim 11 wherein:

the residue stream is substantially all of the methane and lighter components from the feed gas.

13. A method of recovering $C_2$ and heavier hydrocarbon components from a hydrocarbon gas comprising:

(a) separating the feed gas into a first fraction containing substantially methane and lighter components and a second fraction comprised substantially of $C_2$ and heavier components at temperature above $-30.8°$ F.; and (b) separating the residual methane and lighter components from the second fraction at or below $-30.8°$ F. temperatures.

* * * * *

UNITED STATES PATENT AND TRADEMARK OFFICE
CERTIFICATE OF CORRECTION

PATENT NO. : 5,689,032
DATED : November 18, 1997
INVENTOR(S) : William A. Krause; Ronald C. Pasadyn It is certified that error appears in the above-indentified patent and that said Letters Patent is hereby corrected as shown below:

Col. 2, line 34, change "Bette" to --Berre--.
Col. 2, line 54, change "NOx" to --$NO_x$--.
Col. 3, line 8, change "NOx" to --$NO_x$--.
Col. 3, line 52, change "NOx" to --$NO_x$--.
Col. 3, line 56, change "NOx" to --$NO_x$--.
Col. 3, line 61, change "NOx" to --$NO_x$--.
Col. 4, line 18, change "NOx" to --$NO_x$--.
Col. 3, line 66, change "a" to --&--.
Col. 5, line 39, change "C2" to --$C_2$--.
Col. 5, line 66, change "C2" to --$C_2$--.
Col. 6, line 4, change "C2" to --$C_2$--.
Col. 6, line 18, change "C2" to --$C_2$--.
Col. 6, line 43, change "C2" to --$C_2$--.
Col. 6, line 14, add a period at the end of the sentence.
Col. 6, line 62, change "offgas" to --off-gas--.
Col. 8, line 20, change "portions" to --portion--.
Col. 11, line 1, after "separating" insert --at or below -30.8°F.

Signed and Sealed this

Tenth Day of March, 1998

Attest:

BRUCE LEHMAN

Attesting Officer

Commissioner of Patents and Trademarks